United States Patent
Kenda et al.

(10) Patent No.: US 7,112,612 B2
(45) Date of Patent: Sep. 26, 2006

(54) N-ALKYLATED GABA COMPOUNDS, PROCESSES FOR THEIR PREPARATION AND THEIR USE AS MEDICAMENTS

(75) Inventors: Benoit Kenda, Emines (BE); Philippe Michel, Beersel (BE); Luc Quere, Dampicourt (BE)

(73) Assignee: UCB S.A., Brussels (BE)

( * ) Notice: Subject to any disclaimer, the term of this patent is extended or adjusted under 35 U.S.C. 154(b) by 269 days.

(21) Appl. No.: 10/432,115

(22) PCT Filed: Nov. 14, 2001

(86) PCT No.: PCT/EP01/13162

§ 371 (c)(1),
(2), (4) Date: Sep. 29, 2003

(87) PCT Pub. No.: WO02/42256

PCT Pub. Date: May 30, 2002

(65) Prior Publication Data

US 2004/0058991 A1 Mar. 25, 2004

(30) Foreign Application Priority Data

Nov. 21, 2000 (EP) .................................. 00125480

(51) Int. Cl.
*A61K 31/16* (2006.01)
*A61K 31/21* (2006.01)
*A61K 31/275* (2006.01)
*A61K 31/195* (2006.01)
*C07C 233/05* (2006.01)

(52) U.S. Cl. .................. 514/616; 514/513; 514/528; 514/563

(58) Field of Classification Search ................. 564/197, 564/198; 562/561; 560/147, 169, 170; 514/513, 514/528, 563, 616
See application file for complete search history.

(56) References Cited

U.S. PATENT DOCUMENTS

| | | |
|---|---|---|
| 4,639,468 A | 1/1987 | Roncucci et al. |
| 4,696,942 A | 9/1987 | Gobert et al. |
| 4,696,943 A | 9/1987 | Gobert et al. |
| 4,837,223 A | 6/1989 | Gobert et al. |
| 4,837,224 A | 6/1989 | Gobert et al. |
| 4,943,639 A | 7/1990 | Gobert et al. |

FOREIGN PATENT DOCUMENTS

| | | |
|---|---|---|
| EP | 0 162 036 | 11/1985 |
| EP | 0 165 919 | 12/1985 |
| GB | 2 126 224 | 3/1984 |

OTHER PUBLICATIONS

International Search Report for PCT Application No. PCT/EP01/13162, filed Nov. 14, 2001.

*Primary Examiner*—Shailendra Kumar
(74) *Attorney, Agent, or Firm*—McDonnell Boehnen Hulbert & Berghoff LLP

(57) ABSTRACT

The present invention relates to N-alkylated GABA (Gamma-aminobutyric acid) compounds, to processes for their preparation, to their use in therapy and to pharmaceutical compositions containing them. More particularly these compounds are useful for treatment of disorders of the central and/or peripheral nervous system. Of particular interest is their potent anticonvulsant activity.

9 Claims, No Drawings

N-ALKYLATED GABA COMPOUNDS, PROCESSES FOR THEIR PREPARATION AND THEIR USE AS MEDICAMENTS

This application is a National Stage of International Application No. PCT/ EP01/13162, filed Nov. 14, 2001.

N-alkylated GABA compounds, processes for their preparation and their use as medicaments.

The present invention relates to N-alkylated GABA (Gamma-aminobutyric acid) compounds, to processes for their preparation, to their use in therapy and to pharmaceutical compositions containing them. More particularly these compounds are useful for treatment of disorders of the central and/or peripheral nervous system. Of particular interest, is the potent anticonvulsant activity shown by these compounds.

Therefore, these N-alkylated GABA compounds are particularly useful for the prevention and/or the treatment of epilepsy, epileptogenesis, seizure disorders and convulsions. These compounds may also be used for the prevention and/or the treatment of other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, tremor, neonatal cerebral haemorrhage, amyotrophic lateral sclerosis, spasticity, Parkinson's disease and other movement disorders.

Epilepsy is a relatively common neurological condition affecting 0.4–1% of the world's population (45–100 million people). For the general population there are approximately 20–70 new cases per 100,000 diagnosed each year with a 3–5% lifetime probability of developing the disease. Epileptic seizures often cause transient impairment of consciousness, leaving the individual at risk of bodily harm and often interfering with education and employment. The older established antiepileptic drugs (AEDs) phenytoin, carbamazepine, clonazepam, ethosummide, valproic acid and barbiturates are widely prescribed but suffer from a range of side effects. Furthermore, there are significant groups of patients (20–30%) that are resistant to the currently available therapeutic agents. Since 1989 several new drugs have been launched, including felbamate, gabapentin, larnotrigine, oxcarbazepine, tiagabine, topimarate, vigabatrin and zonisamide. While many of the new AEDs show improved efficacies and side-effect profiles, patients with intractable epilepsy remain untreated. There is clearly a need for improved medications (N. D. P. Cosford and al.; Annual Reports in Medicinal Chemistry (1998), 33, p. 61–70). For many years, the agents customarily regarded as anticonvulsant drugs have also been used to treat disorders other than epilepsy (M. J. Eadie, Antiepileptic drugs; Pharmacology and therapeutics, Chapter 23—M. J. Eadie & F. J. E. Vajda, Springer-Verlag Berlin Heidelberg (1999)—Ettore Beghi, The use of anticonvulsants in neurological conditions other than epilepsy; CNS Drugs (1999), 11(1), p. 61–82).

Most anticonvulsant drugs have tranquillising properties, and these probably account for some of the beneficial actions attributed to the drugs.

Over the years, phenytoin has achieved a rather wide area of applications, and is still sometimes employed in managing myotonia, occasional forms of migraine, trigeminal neuralgia, cardiac arrhytnmia and, in recent times, cocaine abuse. Divalproex sodium, a stable compound comprising sodium valproate and valproic acid in a 1:1 molar ratio, is a well known anticonvulsant drug and has been approved by the FDA for the migraine prophylaxis (Mathew NT and col., Migraine prophylaxis with divalproex; Arch. Neurol. (1995), vol. 52, p 281–286). Primidone is employed to suppress essential tremor. Clonazepam is used for some types of non-epileptic myoclonus and for trigeminal neuralgia.

For a number of decades, the treatment of mania and manic recurrences in bipolar disorders has essentially been based on the use of lithium salts ($Li^+$). In recent years, the incomplete protection and tolerance furnished by long-term use of $Li^+$ for bipolar disorders has led to alternative treatments being considered. Clinical studies indicate that during the acute phase of bipolar disorder, up to 40% of patients do not satisfactorily respond to lithium treatment. Yet, one of the most common alternative treatments is the use of anticonvulsants, such as carbamazepine or valproic acid (or its sodium salt), which has been shown to have an antimanic activity and is also capable of having a mood stabilising activity. (Gustavo A. et al., Anticonvulsants for treatment of manic depression; Current Drug Therapy (1989), vol. 56, No. 8).

Chronic and/or neuropathic pains remain the pain syndromes which are the most difficult to treat and there is a genuine need to develop novel active compounds. A number of anticonvulsants, such as valproate or carbamazepine, possess activity in the treatment of these pain conditions (H. L. Fields et al., Excitability Blockers, p 93–116—H. C. Hansen, MD, Treatment of chronic Pain With Antiepileptic Drugs: A New Era; South Medical Journal-Southern Medical Association (1999), 92(7), p 642–649). Carbamazepine and valproate are also the treatment of choice of trigeminal neuralgia or other neuralgia, and may be useful in various painful peripheral neuropathies.

There are suggestions that vigabatrin and gabapentin may have "neuroprotective" actions that may prove useful in neurological disorders where the pathogenic mechanism is thought to involve glutamate-mediated excitotoxicity. These examples illustrate additional ways in which anticonvulsant agents are coming to be employed in contemporary medicine.

Recent pharmacological studies conducted by the applicant have revealed unrecognised and potent pharmacological properties of the herein mentioned novel or known N-alkylated GABA compounds of formula (I), which suggest that they may be useful in treating disorders such as those mentioned above, but not limited to them.

According to one aspect therefore, the present invention provides N-alkylated GABA compounds of formula (I), including pharmaceutically acceptable salts or prodrugs thereof,

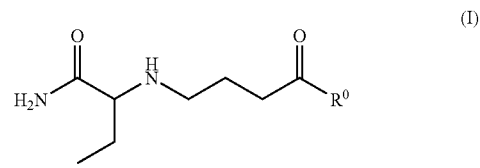

wherein:
$R^0$ is selected from the group consisting of —$OR^1$, —$SR^1$ or —$NR^2R^1$;
$R^1$ and $R^2$ are independently selected from the group consisting of hydrogen, alkyl, alkenyl, alkynyl, cycloalkyl, cycloalkenyl, heterocycle, aryl, arylalkyl, acyl derivatives, imidoyl, amido, ester, oxo and -($L^-$)-$R^3$ or together are -$L^2$-; if $R^0$ is —$NR^2R^1$ then $R^1$ may also be oxy derivatives or amino derivatives;

R³ is selected from the group consisting of cycloalkyl, cycloalkenyl, heterocycle, aryl, oxy derivatives, thio derivatives, amino derivatives, acyl derivatives, acyloxy derivatives, ether, imidoyl, amido, amidooxy, ester, esteroxy, sulfinyl, sulfonyl;

L¹ is a straight or branched alkylene, alkenylene, alkynylene;

L² is a straight or branched alkylene, alkenylene, alkynylene, or one of the foregoing in which one or more methylenes are replaced by —O—, —S— or —NH—;

except the (S) and (R) forms of ethyl 4-{[1-(aminocarbonyl) propyl]amino}butanoate.

In fact, the (S) and (R) forms of ethyl 4-{[1-(aminocarbonyl) propyl]amino}butanoate, compounds of formula (I) in which R⁰ is —O—CH₂—CH₃ has been described respectively in the European Patents No. 0162036 and No 0165919 as a synthesis intermediate. Nevertheless, the pharmaceutically acceptable salts or prodrugs thereof and the racemic form are new and therefore within the scope of formula (I).

The term "alkyl" as used herein, includes saturated monovalent hydrocarbon radicals having straight, or branched moieties or combinations thereof and containing 1–40 carbon atoms, preferably 1–12 carbon atoms. The alkyl group may optionally be substituted with any suitable group, including but not limited to one or more moieties independently selected from the group consisting of halogen, hydroxy, oxo, thiol, amino, nitro, cyano, acyl, acyloxy, sulfonyl, sulfinyl, cycloalklyl, alkenyl, alkynyl, cycloalkenyl, amino derivatives, carboxy, ester, ether, amido, sulfonic acid, phosphonic acid, phosphate, phosphonate, sulfonamide, sulfonyl derivatives, oxycarbonyl derivatives, sulfinyl derivatives, thio derivatives, acyloxy, esteroxy, amidooxy, heterocycle, vinyl, oxy derivatives, aryl. Non-limiting examples of alkyl groups are methyl, ethyl, propyl, 2-propylpentyl, isopropyl, butyl, tertiobutyl, 2,2,2-trimethylethyl, phenethyl, trityl or the same substituted by at least a group selected from halogen, hydroxy, thiol, amino, nitro, cyano, such as trifluoromethyl, trichloromethyl, 2,2,2-trichloroethyl, 1,1-dimethyl-2,2-dibromoethyl, 1,1-dimethyl-2,2,2-trichloroethyl.

The term "lower alkyl", as used herein, and unless otherwise specified, refers to $C_1$ to $C_6$ saturated straight, branched or cyclic hydrocarbon. Non-limiting examples are methyl, ethyl, propyl, isopropyl, butyl, tertiobutyl, pentyl, cyclopentyl, isopentyl, neopentyl, hexyl, isohexyl, cyclohexyl, 3-methylpentyl, 2,2-dimethylbutyl, optionally substituted with any suitable group, including but not limited to one or more moieties selected from groups as described above for the alkyl groups.

The term "alkenyl" refers to an univalent $C_2$ to $C_{12}$ straight or branched, hydrocarbon with at least one double bond, optionally substituted with any suitable group, including but not limited to one or more moieties selected from lower alkyl or other groups as described above for the alkyl groups. Non-limiting examples are ethenyl, 1-propenyl, 2-butenyl, 1,3-butadienyl, 2-pentenyl, isopropenyl, styryl, cinnamyl.

The term "alkynyl" refers to an univalent $C_2$ to $C_{12}$ straight or branched hydrocarbon with at least one triple bond, optionally substituted with any suitable group, including but not limited to one or more moieties selected from lower alkyl or other groups as described above for the alkyl groups. Non-limiting examples are ethynyl, propynyl, 2-penten-4-ynyl, and —C≡—CCH₂-(alkyl) including —C≡—C—CH₂CH₃.

The term "alkylene" refers to an alkyl moiety as described above in which a hydrogen atom has been removed to yield a divalent radical. Non-limiting example is —CH₂—CH (CH₃)—CH₂—.

The term "alkenylene" refers to an alkenyl moiety as described above in which a hydrogen atom has been removed to yield a divalent radical. Non-limiting example is —CH₂—CH═CH—CH₂—.

The term "alkynylene" refers to an alkynyl moiety as described above in which a hydrogen atom has been removed to yield a divalent radical. Non-limiting example is —C≡C—(CH₃)₂—.

The term "cycloalkyl", as used herein, refers to a monovalent group of 3 to 18 carbons derived from a saturated cyclic or polycyclic hydrocarbon such as adamantyl, which can optionally be substituted with any suitable group, including but not limited to one or more moieties selected from lower alkyl or other groups as described above for the alkyl groups. Non-limiting examples are adamantyl, cyclopentyl, cyclohexyl, tricyclo(2.2.1.0)heptanyl.

The term "cycloalkenyl", as used herein, refers to a monovalent group derived from a cyclic or bicyclic hydrocarbon of 3 to 12 carbons that has at least one carbon-carbon double bound or the same which can be substituted with any suitable group, including but not limited to one or more moieties selected from lower alkyl or other groups as described above for the alkyl groups. Non-limiting examples are 2-cyclopenten-1-yl, 2,4-cyclopentadien-1-yl, cyclohexene, 1,3-cyclohexadiene.

The term "heterocycle", as used herein, refers to an aromatic or non aromatic cyclic alkyl, alkenyl, or alkyl moiety as defined above, having at least one O, S and/or N atom interrupting the carbocyclic ring structure and optionally, one of the carbon of the carbocyclic ring structure may be replaced by a carbonyl. Non-limiting examples of aromatic heterocycles are pyridyl, furyl, pyrrolyl, thienyl, isothiazolyl, imiidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thieno (2,3-b)furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, phenanthridinyl, acridinyl, perimidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted as described above for the alkyl groups. Non-limiting examples of non aromatic heterocycles are tetrahydrofuranyl, tetrahydropyranyl, piperidinyl, piperidyl, piperazinyl, imidazolidinyl, morpholino, morpholinyl, 1-oxaspiro(4.5) dec-2-yl, pyrrolidinyl, 2-oxo-pyrrolidinyl, sugar moieties (i.e. glucose, pentose, hexose, ribose, fructose, which may also be substituted) or the same which can optionally be substituted with any suitable group, including but not limited to one or more moieties selected from lower alkyl, or other groups as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkyl group, such as quinuclidinyl, 7-azabicyclo(2.2.1)heptanyl, 7-oxabicyclo(2.2.1)heptanyl, 8-azabicyclo(3.2.1)octanyl.

The term "oxy derivatives", as used herein includes —O—$R^4$ groups wherein $R^4$ is defined below. Non-limiting examples are pentyloxy, allyloxy, methoxy, ethoxy, phenoxy, benzyloxy, 2-naphtyloxy, 2-pyridyloxy, methylenedioxy, carbonate.

$R^4$ and $R^5$ are the same or not and are independently selected from the group consisting of alkyl, alkenyl, alkynyl, cycloalkyl, cycloalkenyl, heterocycle, aryl, arylalkyl or together are -$L^2$- as described above. $R^4$ and $R^5$ can optionally be substituted with any suitable group, including but not limited to one or more moieties selected from lower alkyl or other groups as described above for the alkyl groups.

The term "thio derivative" as used herein, includes —S—$R^4$ groups wherein $R^4$ is defined above.

The term "amino derivatives" as used herein, includes —NH$R^4$ or —N$R^4R^5$ groups wherein $R^4$ and $R^5$ are defined above.

The term "aryl" as used herein, includes an organic radical derived from an aromatic hydrocarbon by removal of one hydrogen, such as phenyl, biphenyl, naphthyl, which can optionally be substituted with any suitable group, including but not limited to one or more moieties selected from lower alkyl or other groups as described above for the alkyl groups. The aryl radical consists of 1–3 rings, preferably one ring, and contains 6–30 carbon atoms preferably 6–10 carbon atoms. Non-limiting examples are phenyl, biphenyl, cumenyl, mesityl, tolyl, xylyl, halophenyl, cyanophenyl, nitrophenyl, methoxyphenyl, naphthyl, indenyl, anthryl.

The term "halogen" as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "amino", as used herein, represents a group of the formula —$NH_2$.

The term "carboxy", as used herein, represents a group of the formula —COOH.

The term "sulfonic acid", as used herein, represents a group of the formula —$SO_3H$.

The term "sulfonamide", as used herein, represents a group of the formula —$SO_2NH_2$ The term "arylalkyl", as used herein, represents a group of the formula -$L^3$-aryl in which $L^3$ is as defined below. Non-limiting examples are benzyl, halobenzyl, cyanobenzyl, methoxybenzyl, nitrobenzyl, 2-phenylethyl, diphenylmethyl, (4-methoxyphenyl) diphenylmethyl, indenyl, anthracenylmethyl.

The term "acyl derivative" as used herein, represents a radical derived from carboxylic acid and thus includes groups of the formula $R^4$—CO—, wherein $R^4$ is defined above and may also be hydrogen. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "acyloxy derivatives" as used herein, represents a radical of carboxylic acid and thus includes groups of the formula $R^4$—CO—O—, wherein $R^4$ is defined above and may also be hydrogen. (possible groups are the same as for acyl derivatives)

The term "imidoyl" as used herein, includes groups of the formula $R^4$—CNH—, wherein $R^4$ is defined above and may also be hydrogen. Non-limiting examples are formimidoyl, hexanimidoyl, succinimidoyl.

The term "sulfonyl" represents a group of the formula —$SO_2$—$R^4$, wherein $R^4$ is defined above.

The term "sulfmyl" represents a group of the formula —SO—$R^4$, wherein $R^4$ is defined above.

The term "oxo" as used herein, represents a group of the formula =O.

The term "ester means a group of formula —COO—$R^4$ wherein $R^4$ is defined above.

The term "esteroxy" means a group of formula —O—COO—$R^4$, wherein $R^4$ is defined above and may also be hydrogen.

The term "ether" means a group selected from $C_1$ to $C_{50}$ straight or branched alkyl, or $C_2$ to $C_{50}$ straight or branched alkenyl or alkynyl groups or a combination of the same, interrupted by one or more oxygen atoms.

$L^3$ and $L^4$ are the same or not and are independently selected from the group of $C_1$ to $C_{12}$ straight or branched alkylene, or $C_2$ to $C_{12}$ straight or branched alkenylene or alkynylene groups.

The term "amido" means a group of formula —$CONH_2$ or —CONH$R^4$ or —CON$R^4R^5$ wherein $R^4$ and $R^5$ are defined above.

The term "amidooxy" means a group of formula —O—$CONH_2$ or —O—CONH$R^4$ or —O—CON$R^4R^5$ wherein $R^4$ and $R^5$ are defined above.

Preferred compounds are the (S) or (R) isomers of formula (II)

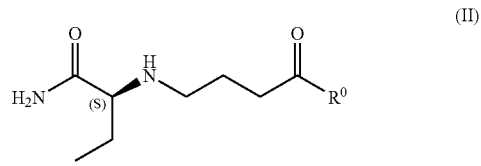

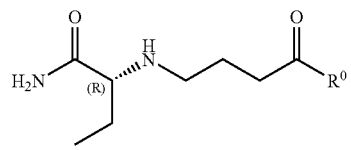

wherein:
R⁰ is selected from the group consisting of —$OR^1$, —$SR^1$ or —$NR^2R^1$;
$R^1$ and $R^2$ are independently selected from the group consisting of hydrogen, alkyl, alkenyl, alkynyl, cycloalkyl, cycloalkenyl, heterocycle, aryl, arylalkyl, acyl derivatives, imidoyl, amido, ester, oxo and -($L^4$)-$R^3$ or together are -$L^2$-; if $R^0$ is —$NR^2R^1$ then $R^1$ may also be oxy derivatives or amino derivatives;

$R^3$ is selected from the group consisting of cycloalkyl, cycloalkenyl, heterocycle, aryl, oxy derivatives, thio derivatives, amino derivatives, acyl derivatives, acyloxy derivatives, ether, imidoyl, amido, amidooxy, ester, esteroxy, sulfinyl, sulfonyl;

$L^1$ is a straight or branched alkylene, alkenylene, alkynylene;

$L^2$ is a straight or branched alkylene, alkenylene, alkynylene, or one of the foregoing in which one or more methylenes are replaced by —O—, —S— or —NH—;

except the (S) and (R) forms of ethyl 4-{[1-(aminocarbonyl)propyl]amino}butanoate.

Most preferred compounds are the (S) isomers of formula (II)

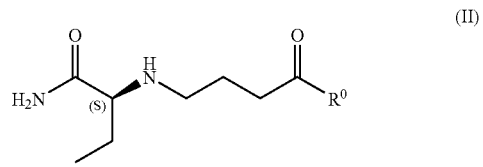

in which $R^0$ is as defined above.

The best results have been obtained with the (S) isomers of formula (II) in which:
$R^0$ is —$OR^1$ or $SR^1$;
$R^1$ is selected from the group consisting of ($C_1$–$C_8$) alkyl, ($C_1$–$C_{10}$) cycloalkyl, $C_6$ aryl, and $L^1$-$R^3$;
$L^1$ is a ($C_1$–$C_7$) alkylene;
$R^3$ is ($C_1$–$C_{10}$) alkyl, ($C_1$–$C_{10}$) cycloalkyl, or $C_6$ aryl.

In the following Table 1, non-limiting examples of preferred compounds are listed:

TABLE 1

| Compound No. | Structure | Configuration | Chemical name (IUPAC) |
| --- | --- | --- | --- |
| A | 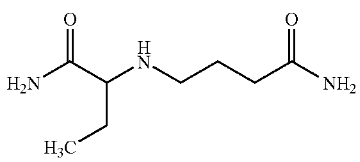 | S | 4-{[(1S)-1-(aminocarbonyl)propyl]amino}butanamide |
| B | 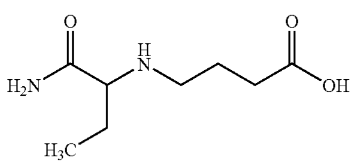 | S | 4-{[(1S)-1-(aminocarbonyl)propyl]amino}butanoic acid |
| C | 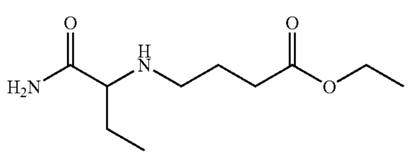 | rac | ethyl 4-{[1-(aminocarbonyl)propyl]amino}butanoate |
| F | 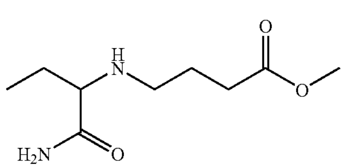 | S | methyl 4-{[(1S)-1-(aminocarbonyl)propyl]amino}butanoate |
| G | 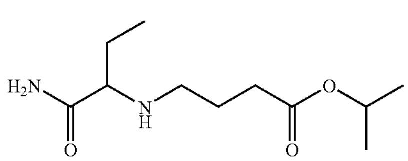 | S | isopropyl 4-{[(1S)-1-(aminocarbonyl)propyl]amino}butanoate |
| H | 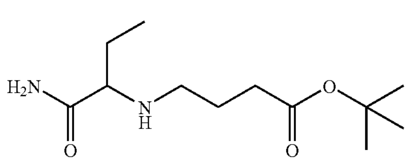 | S | tertiobutyl 4-{[(1S)-1-(aminocarbonyl)propyl]amino}butanoate |

TABLE 1-continued

| Compound No. | Structure | Configuration | Chemical name (IUPAC) |
| --- | --- | --- | --- |
| I | 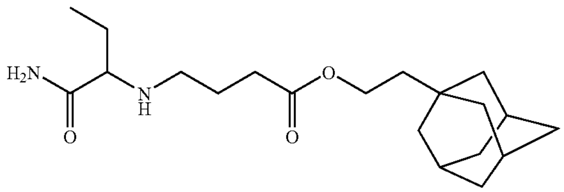 | S | 2-(1-adamantyl)ethyl 4-{[(1S)-1-(aminocarbonyl)propyl]amino}butanoate |
| J | 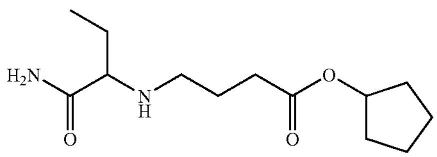 | S | cyclopentyl 4-{[(1S)-1-(aminocarbonyl)propyl]amino}butanoate |
| K | 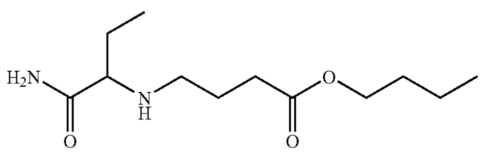 | S | butyl 4-{[(1S)-1-(aminocarbonyl)propyl]amino}butanoate |
| L | 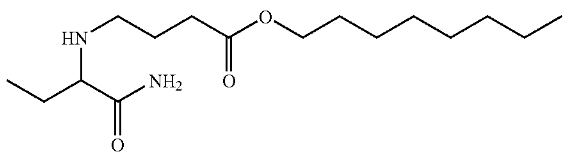 | S | octyl 4-{[(1S)-1-(aminocarbonyl)propyl]amino}butanoate |
| M | 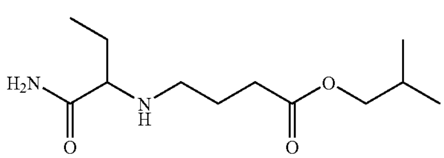 | S | isobutyl 4-{[(1S)-1-(aminocarbonyl)propyl]amino}butanoate |
| N | 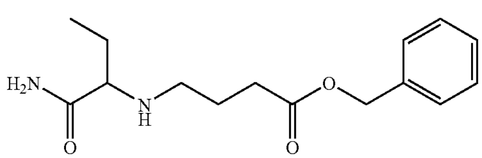 | S | benzyl 4-{[(1S)-1-(aminocarbonyl)propyl]amino)butanoate |
| O | 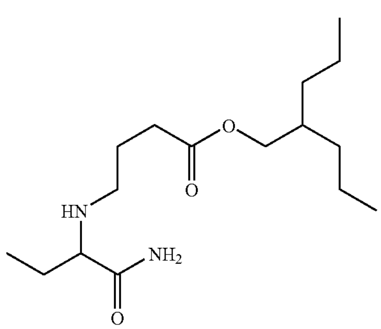 | S | 2-propylpentyl 4-{[(1S)-1-(aminocarbonyl)propyl]amino}butanoate |
| P | 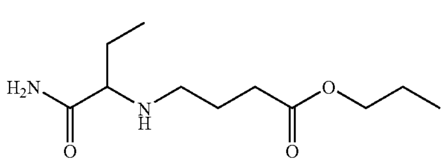 | S | propyl 4-{[(1S)-1-(aminocarbonyl)propyl]amino}butanoate |

TABLE 1-continued

| Compound No. | Structure | Configuration | Chemical name (IUPAC) |
| --- | --- | --- | --- |
| Q | 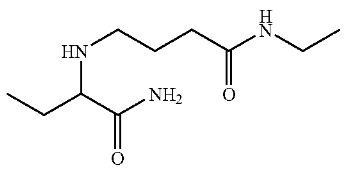 | S | (2S)-2-{[4-(ethylamino)-4-oxobutyl]amino}butanamide |
| R | 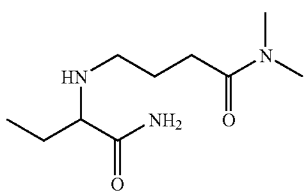 | S | (2S)-2-{[4-(dimethylamino)-4-oxobutyl]amino}butanamide |
| S | 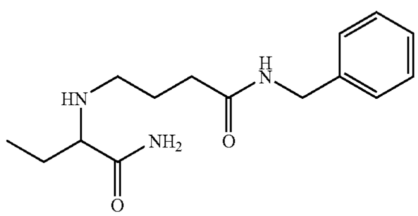 | S | (2S)-2-{[4-(benzylamino)-4-oxobutyl]amino}butanamide |
| T | 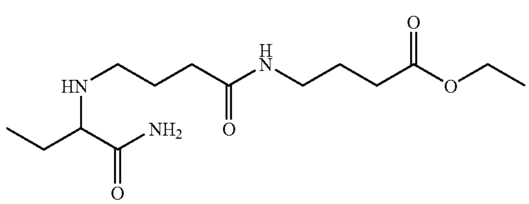 | S | ethyl 4-[(4-{[(1S)-1-(aminocarbonyl)propyl]amino}butanoyl)amino]butanoate |
| U | 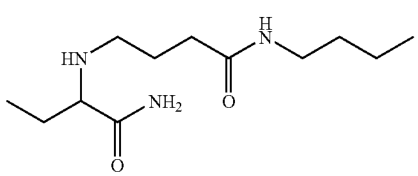 | S | (2S)-2-{[4-(butylamino)-4-oxobutyl]amino}butanamide |
| V | 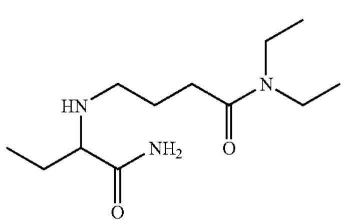 | S | (2S)-2-{[4-(diethylamino)-4-oxobutyl]amino}butanamide |
| W | 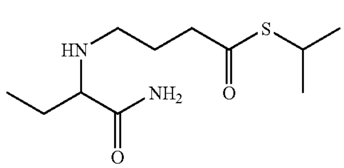 | S | S-isopropyl 4-{[(1S)-1-(aminocarbonyl)propyl]amino}butanethioate |

The most preferred compounds are the compounds numbered A, B, C, D, E, F, G, H, I, J, K, L, M, N, O, P and W.

For the above-mentioned compounds, the preferred pharmaceutically acceptable salts are the hydrobromides or hydrochlorides.

By "rac" the applicant means the racemic form.

The invention includes within its scope all the possible salts or complexes and particularly pharmaceutically acceptable salts of the compounds of the present invention.

The invention also includes within its scope all the possible isomers, stereoisomers, enantiomers, racemate, optical isomers and their mixtures and the metabolites and the metabolic precursors (or bioprecursors, otherwise known as pro-drug) of the compounds of formula (I).

As used herein, the term "pharmaceutically acceptable salts" or complexes refers to either an acid addition salt or a base addition salt that retains the desired biological activity of the above-identified compounds and exhibit minimal or no toxicological effects. Pharmaceutically acceptable salts are well known in the art. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as fumaric acid, acetic acid, tartaric acid, succinic acid, malic acid, fumaric acid, ascorbic acid, benzoic acid, tannic acid, pamoic acid, alginic acid, polyglutamic acid, napthalenesulfonic acid, napthalenedisulfonic acid, and polygalacturonic acid.

The term "stereoisomers" is a general term for all isomers of the individual molecules that differ only in the orientation of their atoms in space. It includes mirror image isomers (enantiomers), geometric (cis/trans or Z/E) isomers and isomers of compounds with more than one chiral centre that are not mirror images of another (diastereomers). Compounds where asymmetric or chiral centers are present, are designated by the symbols "R" or "S", depending on the configuration of substituents around the chiral carbon atom. The present invention contemplates various stereoisomers and mixtures thereof. The invention includes enantiomers, diastereomers and equal mixture of enantiomers designated as racemic mixture (+/−). Individual stereoisomers of compounds of the present invention can be prepared synthetically from commercially available starting materials which contain asymmetric or chiral centers or by the use of enantioselective reactions or by preparation of racemic mixture followed by resolution well-known to those of ordinary skill in the art. Geometric isomers can also exist in the compounds of the present invention. The present invention contemplates the various geometric isomers and mixtures thereof resulting from the arrangement of substituents around a carbon-carbon double bound or arrangement of substituents around a ring. Substituents around a carbon-carbon double bond are designated as being in the Z or E configuration (E. L. Eliel and S. H. Wilen, Stereochemistry of Organic Compounds; Wiley-Interscience (1994), p. 1197). The arrangement of substituents around a ring are designated as cis or trans where the term "cis" represents substituents on the same side of the plane of the ring and the term "trans" represents substituents on opposite sides of the plane of the ring. Mixtures of compounds where the substituents are disposed on both the same and opposite sides of plane of the ring are designated cis/trans.

The term "prodrug" represents compounds which are rapidly transformed in vivo to the parent compound of the above formula (1), for example, by hydrolysis in blood.

Prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialldysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

The present invention further provides a method for the synthesis of compounds of formula (I) according to the following schemes.

The following experimental procedures are representative for the synthesis of compounds (I) or (II) depending on the choice of the absolute configuration of the 2-amino-butanamide (IV).

For the synthesis of compounds of general formula (I) or (II) as defined above wherein $R^0$ is $OR^1$, $R^1$ having the same meaning as stated above, a compound of formula (III) is reacted with 2-amino-butanamide of formula (IV) (1 to 2 equivalents) according to the equation:

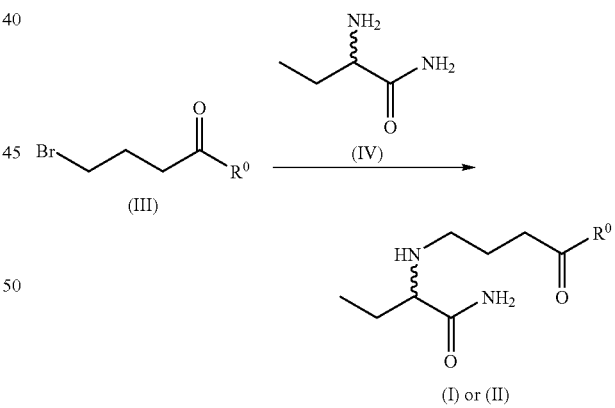

This reaction may be carried out under inert atmosphere, in a solvent like dimethylformamide, acetonitrile, toluene or dichloromethane, in the presence or not of a base, and between −5° C. and 100° C.

As an alternative, in order to obtain the compound of formula (I) or (II) in which $R^0$ represents —OH, the corresponding compound of formula (I) wherein $R^0$ represents —$OR^1$ is selectively hydrolysed by an acid or by a base under any appropriate conditions known to the person skilled in the art. As an example, the reaction may be carried out in an aqueous solution of HCl, between 0° C. and 70° C.

Starting material, compound of formula (III), may be prepared by reacting a 4-halobutyryl halide of formula (V) in which $X^1$ and $X^2$ represent a halogen atom, with a compound of formula $R^0H$ in which $R^0$ is as defined above, according to the following equation

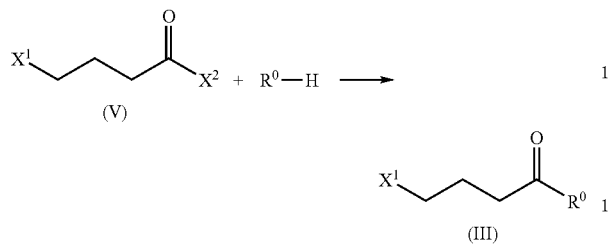

This reaction may be carried out in an inert solvent, for example dichloromethane, at a temperature of about 0° C., in the presence of a base, for example pyridine or triethylamine. Alternatively, this reaction may be carried out without the inert solvent.

For the synthesis of compounds of general formula (I) or (II) wherein $R^0$ represents $-SR^1$ or $-NR^1R^2$, $R^1$ and $R^2$ having the same meanings as stated above, compound (I) or (II) in which $R^0$ is $OR^1$ is N-protected by a suitable chemical group to give compound (VI) wherein $R^0$ is $-OR^1$. This group, such as a benzyloxycarbonyl, can be introduced under any appropriate conditions known to the person skilled in the art (Kociensky, P. J. in "Protecting Group" Georg Thieme Verlag, Stuttgart, 1994). Selective hydrolysis of the ester (VI) in mild acidic conditions (for example dilute hydrochloric acid) with or without an organic cosolvent leads to the acid (VI)

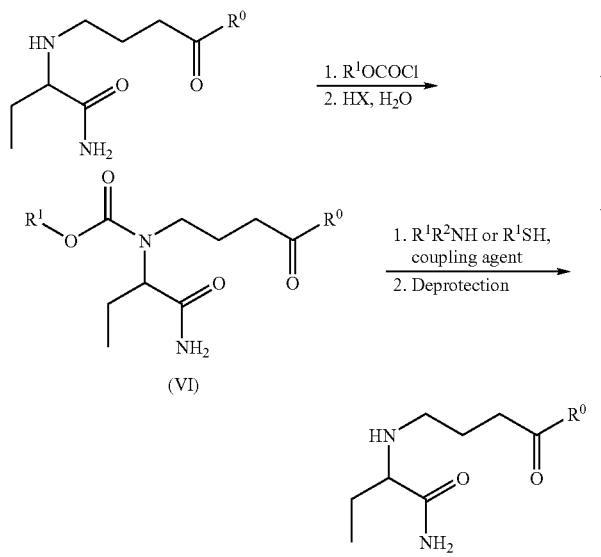

in which $R^0$ is OH.

The coupling with an amine $HNR^1R^2$ or a thiol $-SR^1$, $R^1$ and $R^2$ having the same meanings as stated above, is performed using standard conditions of peptidic coupling known to the person skilled in the art (Bodanszky, A.; Bodanszky, M. "The practice of Peptide Synthesis" Springer Verlag, 1984). The compounds of formula (VI) where $R^0$ represents $-NR^1R^2$ can be deprotected under any appropriate conditions known to the person skilled in the art, for example by hydrogen in the presence of Pd on charcoal (Kociensky, P. J. in "Protecting Group" Georg Thieme Verlag, Stuttgart, 1994). The compounds of formula (VI) where $R^0$ represents $-SR^1$ can be deprotected selectively in acidic conditions using for example trifluoroacetic acid or boron trifluoride etherate and ethanethiol (Kociensky, P. J. in "Protecting Group" Georg Thieme Verlag, Stuttgart, 1994).

In another aspect, the invention provides compounds of formula (I) including the (S) and (R) forms of ethyl 4-{[1-(aminocarbonyl)propyl]amino}butanoate and the pharmaceutically acceptable salts thereof for their use as medicament.

Accordingly, the invention concerns N-alkylated GABA compounds of formula (I),

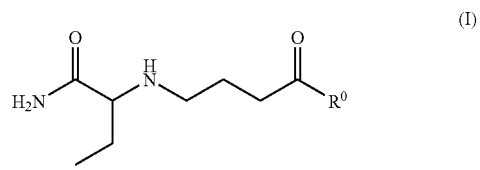

including pharmaceutically acceptable salts or prodrugs thereof, wherein:
  $R^0$ is selected from the group consisting of $-OR^1$, $-SR^1$ or $-NR^2R^1$;
  $R^1$ and $R^2$ are independently selected from the group consisting of hydrogen, alkyl, alkenyl, alkynyl, cycloalkyl, cycloalkenyl, heterocycle, aryl, arylalkyl, acyl derivatives, imidoyl, amido, ester, oxo and -($L^1$)-$R^3$ or together are -$L^2$-; if $R^0$ is $-NR^2R^1$ then $R^1$ may also be oxy derivatives or amino derivatives;
  $R^3$ is selected from the group consisting of cycloalkyl, cycloalkenyl, heterocycle, aryl, oxy derivatives, thio derivatives, amino derivatives, acyl derivatives, acyloxy derivatives, ether, imidoyl, amido, amidooxy, ester, esteroxy, sulfinyl, sulfonyl;
  $L^1$ is a straight or branched alkylene, alkenylene, alkynylene;
  $L^2$ is a straight or branched alkylene, alkenylene, alkynylene, or one of the foregoing in which one or more methylenes are replaced by $-O-$, $-S-$ or $-NH-$;

including the (S) and (R) forms of ethyl 4-{[1-(aminocarbonyl)propyl]amino}butanoate for their use as medicament.

It has finally been found that compounds of formula (I) and the pharmaceutically acceptable salts thereof, are particularly effective anticonvulsant agents.

Therefore, these compounds are particularly useful for the prevention and/or the treatment of epilepsy, epileptogenesis, seizure disorders and convulsions.

These compounds may also be used for the prevention and/or the treatment of other neurological disorders including bipolar disorders, mania, depression, anxiety, migraine, trigeminal and other neuralgia, chronic pain, neuropathic pain, cerebral ischemia, cardiac arrhythmia, myotonia, cocaine abuse, stroke, myoclonus, tremor, neonatal cerebral haemorrhage, amyotrophic lateral sclerosis, spasticity, Parkinson's disease and other movement disorders.

Thus, the present invention in a further aspect concerns the use of compounds of formula (I) or the pharmaceutically acceptable salts or prodrugs thereof as defined above, for the manufacture of a medicament for the treatment and/or prophylaxis of neurological disorders such as mentioned above.

In particular, the present invention concerns the use of compounds of formula (I) and the pharmaceutically acceptable salts thereof as defined above, for the manufacture of a medicament for the treatment and/or prophylaxis of epilepsy, bipolar disorders, chronic pain or neuropathic pain and migraine.

It has been surprisingly determined that the activity and properties of the active compounds, including anticonvulsant activity, oral availability and stability in vitro or in vivo can vary significantly among the optical isomers of the disclosed compounds.

In a preferred embodiment, the active compound or its prodrug is administered in an enantiomerically enriched form, i.e., substantially in the form of one isomer.

Therefore, in a preferred embodiment, the present invention concerns the use of (S) enantiomers of formula (II) including the (S) form of ethyl 4-{[1-(aminocarbonyl)propyl]amino}butanoate and the pharmaceutically acceptable salts thereof as defined above, for the manufacture of a medicament for the treatment and/or prophylaxis of epilepsy, bipolar disorders, chronic pain or neuropathic pain and migraine.

The present invention also concerns a method for treating epilepsy, migraine, bipolar disorders, chronic pain or neuropathic pain, in a mammal in need of such treatment, comprising administering a therapeutic dose of at least one compound of formula (I) or (II) and the pharmaceutically acceptable salts thereof to a patient.

The methods of the invention comprise administration to a mammal (preferably human) suffering from above mentioned diseases, of a pharmaceutical composition according to the invention in an amount sufficient to alleviate the condition. The compound is conveniently administered in any suitable unit dosage form, including but not limited to one containing 100 to 4000 mg, preferably 250 to 1500 mg of active ingredient per unit dosage form.

The term "treatment" as used by the Applicant means curative treatment and prophylactic treatment.

By "curative" we mean the efficaciousness of formula (I) or (II) in treating the current episode (e.g., like a manic phase or a depressive phase in bipolar disorders).

By "prophylactic" or "maintenance" we mean the prevention of the recurrence of epilepsy, manic/depressive, migraine, chronic pain or neuropathic pain episodes.

The term "epilepsy" as used by the Applicant refers to a disorder of brain function characterised by the periodic and unpredictable occurrence of seizures. Seizures can be "non-epileptic" when evoked in a normal brain by treatments such as electroshock or chemical convulsants or "epileptic" when evoked without evident provocation.

The term "seizure" refers to a transient alteration of behaviour due to the disordered, synchronous, and rhythmic firing of populations of brain neurones.

The term "migraine" as used by the Applicant means a disorder characterised by recurrent attacks of headache that vary widely in intensity, frequency, and duration. The attacks are commonly unilateral and are usually associated with anorexia, nausea, vomiting, phonophobia, and/or photophobia. In some cases they are preceded by, or associated with, neurological and mood disturbances. Migraine headache may last from 4 hours to about 72 hours. The International Headache Society (IHS, 1988) classifies migraine with aura (classical migraine) and migraine without aura (common migraine) as the major types of migraine.

Migraine with aura consists of a headache phase preceded by characteristic visual, sensory, speech, or motor symptoms. In the absence of such symptoms, the headache is called migraine without aura.

The term "bipolar disorders" as used by the Applicant is defined below.

Bipolar disorders are classified as Mood Disorders according to the Diagnostic and Statistical Manual of Mental Disorders, 4th edition (Diagnostic and Statistical Manual of Mental Disorders (DSM-IV TM), American Psychiatry Association, Washington, D.C., 1994). Bipolar disorders are generally characterised by spontaneously triggered repeated (i.e. at least two) episodes in which the patient's hyperexcitability, activity and mood are significantly disturbed, this disturbance consisting on some occasions of an elevation of mood and increased energy and activity (mania or hypomania), and in other occasions a lowering of mood and decreased energy and activity (depression). Bipolar disorders are separated into four main categories in the DSM-IV (bipolar I disorder, bipolar II disorder, cyclothymia, and bipolar disorders not otherwise specified).

By "manic episode", the applicant means a distinct period during which there is an abnormally and persistently elevated, expansive, or irritable mood with signs of pressured speech and psychomotor agitation.

By "hypomania", the applicant means a less extreme manic episode, with lower grade of severity.

By "major depressive episode", the applicant means a period of at least 2 weeks during which there is either depressed mood or the loss of interest or pleasure in nearly all activities with signs of impaired concentration and psychomotor retardation.

By "mixed episode", the applicant means a period of time. (lasting at least 1 week) in which the criteria are met both for a manic episode and for a major depressive episode nearly every day.

The term "chronic pain" as used by the Applicant is gradually being recognised as a disease process distinct from acute pain. Conventionally defined as pain that persists beyond the normal time of healing, pain can also be considered chronic at the point when the individual realises that the pain is going to be a persistent part of their lives for the foreseeable future. It is likely that a majority of chronic pain syndromes involves a neuropathic component, which is usually harder to treat than acute somatic pain The term "neuropathic pain" as used by the Applicant, is a pain initiated by a pathological change in a nerve which signals the presence of a noxious stimulus when no such recognisable stimulus exists, giving rise to a false sensation of pain. In other words, it appears that the pain system has been turned on and cannot turn itself off.

The potent activity of the compounds of formula (I) or (II), or their pharmaceutically acceptable salts, as anticonvulsants was evidenced by audiogenic seizures test induced in sound-susceptible mice. These examples illustrate the invention without in any way limiting its scope. The objective of the following pharmacological test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, p. 145–181; Buchhalter J. R., Epilepsia (1993), 34, S31–S41). The results obtained with the tested compounds of formula (I) and (II) show a strong pharmacological effect (see Table 4).

For treating diseases, compounds of formula (I) or (II) including the (S) and (R) forms of ethyl 4-{[1-(aminocarbonyl)propyl]amino}butanoate, or their pharmaceutically acceptable salts, may be employed at an effective daily dosage and administered via a pharmaceutical composition.

Therefore, another embodiment of the present invention is a pharmaceutical composition that includes an effective amount of a compound of formula (I) or (II) including the (S) and (R) forms of ethyl 4-{[1-(aminocarbonyl)propyl]amino}butanoate, or its pharmaceutically acceptable salts or derivative in combination with a pharmaceutically acceptable carrier for any of the disorders described herein.

To prepare the pharmaceutical composition of this invention, one or more of the N-alkylated GABA compounds of formula (I) or (II), or their pharmaceutically acceptable salts, are intimately admixed with a pharmaceutical carrier according to conventional pharmaceutical compounding techniques, which carrier may take a wide variety of forms depending on the form of preparation desired for administrating, e.g., oral, rectal, or parenteral.

The present invention requires administration of an effective dose of N-alkylated GABA compounds for the treatment and/or the prophylaxis of epilepsy, bipolar disorders, migraine and chronic pain or neuropathic pains. The dose required in accordance with the invention should be sufficiently high to permit the relief of epilepsy, bipolar disorders, migraine and chronic pain or neuropathic pains. Pharmaceutical compositions comprising N-alkylated GABA compounds can, for example, be administered orally or parenterally, i.e., intravenously, intramuscularly or subcutaneously, intrathecally.

Pharmaceutical compositions which can be used for oral administration can be solids or liquids and can, for example, be in the form of tablets, pills, dragees, gelatin capsules, solutions, syrups, and the like.

To this end, N-alkylated GABA compounds can be used mixed with an inert diluent or a non-toxic pharmaceutically acceptable vehicle such as starch or lactose, for example. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

They also comprise compositions which can release the active substance in a controlled manner. Pharmaceutical compositions which can be used for parenteral administration are in the pharmaceutical forms which are known for this mode of administration and are in the form of aqueous or oily solutions or suspensions generally contained in ampoules, disposable syringes, glass or plastics vials or infusion containers.

In addition to the active compound, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The percentage of compound of formula (I) or (II) in the pharmaceutical compositions can fall within a wide range of concentrations and depends on a variety of factors such as the patient's sex, age, weight and medical condition, as well as on the method of administration. Thus the quantity of compound of formula (I) or (II) in compositions for oral administration is at least 0.5% by weight and can be up to 80% by weight with respect to the composition weight. The terms active material" and "active product" as used by the Applicant mean N-alkylated GABA compounds alone or combined with at least one other pharmaceutically active compound for use in these pathologies. Non-limiting examples of these compounds which can be cited for use in combination with N-alkylated GABA compounds are antivirals, antispastics (i.e.: baclofen), antiemetics, antimanic mood stabilizing agents, analgesics (i.e.: aspirin, ibuprofen, paracetamol), narcotic analgesics, topical anesthetics, opioid analgesics, lithium salts, antidepressants (i.e.: mianserin, fluoxetine, trazodone), tricyclic antidepressants (i.e.: imipramine, desipramine), anticonvulsants (i.e.: valproic acid, carbamazepine, phenytoin . . . ), antipsychotics (i.e.: risperidone, haloperidol), neuroleptics, benzodiazepines (i.e.: diazepam, clonazepam), phenothiazines (i.e.: chlorpromazine), calcium channel blockers, amphetamine, clonidine, lidocaine, mexiletine, capsaicin, caffeine, quetiapine, serotonin antagonists, α-blockers, antiarrhythmics, triptans, ergot derivatives.

Especially, the present invention also concerns a pharmaceutical composition comprising at least one of the herein disclosed N-alkylated GABA compounds of formula (I) or (II) including the (S) and (R) forms of ethyl 4-{[1-(aminocarbonyl)propyl]amino}butanoate and at least one compound inducing neural inhibition mediated by the $GABA_A$ receptors.

By compounds inducing neural inhibition mediated by the $GABA_A$ receptors, we understand the following compounds: benzodiazepines, barbiturates, steroids, and anticonvulsants such as valproate, viagabatrine, tiagabine, or pharmaceutical acceptable salts thereof.

Benzodiazepines include the 1,4 benzodiazepines, such as diazepam and clonazepam, and the 1,5 benzodiazepines, such as clobazam. Preferred compound is clonazepam.

Barbiturates include phenobarbital and pentobarbital. Preferred compound is phenobarbital.

Steroids include adrenocorticotropic hormones such as tetracosactide acetate, etc.

Anticonvulsants include hydantoins (phenytoin, ethotoin, etc), oxazolidines (timethadione, etc.), succinimides (ethosumi de, etc.), phenacemides (phenacemide, acetylphenetu-ride, etc.), sulfonamides (sulthiame, acetoazolamide, etc.), aminobutyric acids (e.g. gamma-amino-beta-hydroxybutyric acid, etc.), sodium valproate and derivatives, carbamazepine and so on.

Preferred compounds include valproic acid, valpromide, valproate pivoxil, sodium valproate, semi-sodium valproate, divalproex, clonazepam, phenobarbital, vigabatrine, tiagabine.

For the preferred oral compositions, the daily dosage is in the range 100 to 3000 milligrams (mg) of compounds of formula (I) or (II).

In compositions for parenteral administration, the quantity of compound of formula (I) or (II) present is at least 0.5% by weight and can be up to 33% by weight with respect to the composition weight. For the preferred parenteral compositions, the dosage unit is in the range 1 mg to 1000 mg of compounds of formula (I) or (II).

The daily dose can fall within a wide range of dosage units of compound of formula (I) or (II), and is generally in the range 100 to 3000 mg. However, it should be understood that the specific doses can be adapted to particular cases depending on the individual requirements, at the physician's discretion.

The amount of the active ingredients (compound (I) or (II) and compound inducing neural inhibition mediated by the $GABA_A$ receptors) in the pharmaceutical composition of the invention will vary depending on the mammal to which the compositions are administered, the disease to be treated, other active ingredients present, etc. Generally, the amount of the compound inducing neural inhibition mediated by the $GABA_A$ receptors and the amount of compound (I) or (II) for a given composition and dosage form can be readily determined employing routine procedures.

The above examples illustrate but do not limit the possible compositions containing the active compounds which have to be delivered.

The following examples illustrate but do not limit the invention.

EXAMPLE 1

Compounds of Formula III: "Cyclopentyl 4-bromo-butanoate"

4-Bromo-butyric acid esters are known (see Table 2) or have been synthesized according to a general procedure. The physico-chemical properties of the new compounds are listed in table 2.

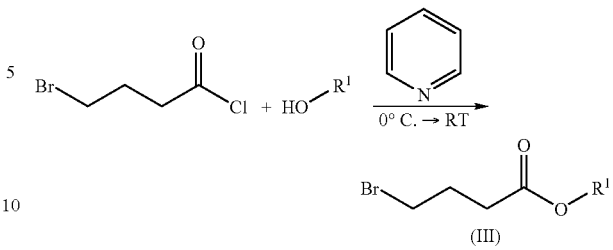

The synthesis of cyclopentyl 4-bromo-butanoate is a typical example:

In a three necked flask under nitrogen, cyclopentanol ($R^0$=O—$R^1$ and $R^1$=$C_5H_9$) (2.9 ml, 0.032 mole, available from commercial sources) was added dropwise to a stirred solution of 4-bromo-butyryl chloride (3 ml, 0.026 mole, available from commercial sources) and pyridine (2.1 ml, 0.026 mole) cooled at 0° C. The white suspension was stirred at room temperature (RMI for 20 h, dissolved in dichloromethane, washed with 1N HCl. The organic phase was dried over magnesium sulfate, filtered and concentrated in vacuum (20 mm Hg) to afford 5.98 g of cyclopentyl 4-bromo-butanoate. The compound was used directly in the next alkylation step without further purification.

The other 4-Bromo-butyric acid esters of formula (III) listed in Table 2, which includes the corresponding physico-chemical properties, the same synthesis scheme has been followed. The above examples illustrate but do not limit the invention.

TABLE 2

| With $R^0$ = $OR^1$ and $R^1$ = | Name | Reference/Physico-Chemical properties |
|---|---|---|
| Methyl | Methyl 4-bromo-butanoate | Hand, E. S.; Johnson, S. C.; Baker, D. C. J. Org. Chem 1997, 62, 1348–1355. |
| Isopropyl | Isopropyl 4-bromo-butanoate | $^1$H-NMR(DMSO): 1.20(d, 6H); 2.05 (m, 2H); 2.40(t, 2H); 3.55(t, 2H); 4.90 (hept, 1H). |
| Tertiobutyl | Tertiobutyl 4-bromo-butanoate | $^1$H-NMR(DMSO): 1.42(s, 9H); 2.05 (m, 2H); 2.35(t, 2H); 3.50(t, 2H). |
| 2-(1-adamantyl)ethyl | 2-(1-adamantyl)ethyl 4-bromo-butanoate | MS (GC/MS): 328/330(M$^+$·) |
| Cyclopentyl | Cyclopentyl 4-bromo-butanoate | MS (GC/MS): 234/236(M$^+$·) |
| n-Butyl | n-butyl 4-bromo-butanoate | Siggins, J. E.; Ackerman, J. H.; Larsen, A. A. J. Med. Chem 1965, 8, 728. |
| n-Octyl | n-Octyl 4-bromo-butanoate | MS (GC/MS): 279/281(M$^+$·) |
| Isobutyl | Isobutyl 4-bromo-butanoate | MS (GC/MS): 223/225(M$^+$·) |
| Benzyl | Benzyl 4-bromo-butanoate | Baba, A.; Kawamura, N.; Makino, H.; Ohta, Y.; Taketomi, S. et al J. Med. Chem 1996, 39, 5176–5182. |
| 2-Propylpentyl | 2-Propylpentyl 4-bromo-butanoate | MS (GC/MS): 279/281(M+.) |
| n-Propyl | n-Propyl 4-bromo-butanoate | Siggins, J. E.; Ackerman, J. H.; Larsen, A. A. J. Med. Chem 1965, 8, 728. | d = doublet,
t = triplet,
m = multiplet,
s = singlet,
hept = heptuplet.

EXAMPLE 2

Synthesis of Preferred COMPOUNDS of Formula (I) or (II) with $R^0$=—O—$R^1$

In a three necked flask under argon, cyclopentyl 4-bromobutanoate ($R^0$=—O—$R^1$ and $R^1$=—$C_5H_9$) (5.98 g; 0.025 mole) was added dropwise to a solution of (S)-2-aminobutanamide (5.20 g; 0.051 mole; For a synthesis: Folkers, K. et al J. Med. Chem. 1971, 14, p. 484–487) in dimethylformamide (DMF, 50 ml) at room temperature. The solution was stirred at this temperature for 20 h. The solvent was then evaporated under vacuum. The crude mixture was

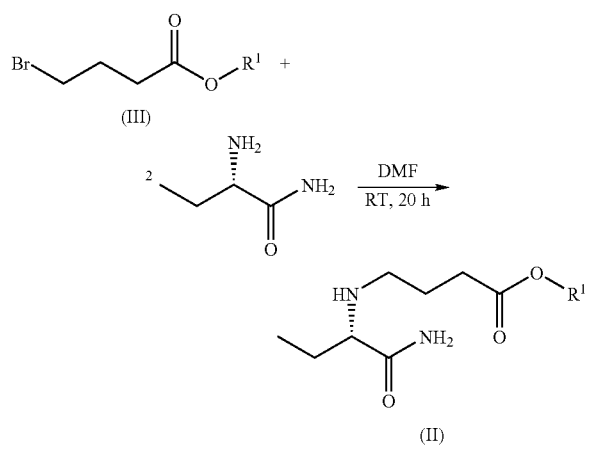

dissolved in dichloromethane, the solid filtered off and the solution was washed with a 10% aqueous sodium bicarbonate. The aqueous phase was extracted twice with dichloromethane. The combined organic phases were dried over magnesium sulfate, filtered and evaporated under vacuum (20 mm Hg). The crude product was dissolved in diethylether and 1.5 equivalent of HCl dissolved in diethylether was added. The white precipitate was filtered, dried under vacuum (1 mm Hg) to afford 6.07 g of cyclopentyl 4-{[(1S)-1-(aminocarbonyl)propyl]amino}butanoate hydrochloride as a white powder.

For the other compounds of formula (I) or (II), some of which have been listed in table 3, the same synthesis scheme has been followed.

EXAMPLE 3

Compound with $R^0$=—$NH_2$

Aminolysis of GABA ester of formula (I) or (II) in which $R^0$ is —O—$CH_3$ or —O—$CH_2$—$CH_3$.

In a three necked flask, gazeous $NH_3$ is bubbled through a solution of ethyl 4-{[(1S)-1-(aminocarbonyl)propyl]amino}butanoate (5 g, 0.019 mol.) in MeOH for 33 h and the solvent is evaporated. The crude amide is purified by preparative HPLC on silicagel ($CH_2Cl_2$/MeOH/$NH_4OH$): 9/0.9/0.1 v/v). The free amine is dissolved in MeOH and a methanolic solution of HCl (2.3 M, 1.62 ml) is added. After 0.5 h, the solvent is evaporated in vacuo and the crude salt is recrystallised in EtOH to afford the final hydrochloride (0.33 g).

EXAMPLE 4

Compound with $R^0$=OH

Hydrolysis of ethyl 4-{[(1S)-1-(aminocarbonyl)propyl]amino}butanoate.

In a three neck flask under argon, a solution of ethyl 4-{[(1S)-1-(aminocarbonyl) propyl]amnino}butanoate (2 g, 0.008 mol.) in HCl 2N is heated for 0.2 h at 55° C., cooled down to room temperature and the aqueous solution is lyophilized. The solid is triturated in acetonitrile, filtered and dried under vacuo to afford the acid (1.2 g) as a white solid.

For the other N-alkylated esters of formula (I) or (II) listed in Table 3, including the corresponding physico-chemnical properties, the synthetic strategies described earlier have been followed. The examples in the table below illustrate but do not limit the invention.

TABLE 3

| Compound No. | Salt | Configuration | Analysis/Reference |
|---|---|---|---|
| A | HCl | S | MS (LC/MS APCI+): 188($MH^+$) |
| B | HCl | S | MS (LC/MS APCI+): 189($MH^+$). |
| C | HBr | racemic | $^1$H-NMR (DMSO): 0.87(t, 3H); 1.15(t, 3H); 1.70–1.95 (m, 4H); 2.38(t, 2H); 2.81(m, 2H); 3.66(dd, 1H); 4.30 [q, 2H]7.59(s, 1H); 7.88(s, 1H); 8.62 (broad s, 2H). MS (LC/MS APCI+): 217($MH^+$). |
| D | HCl | S | Described in: European Patent No 0162036 |
| E | HCl | R | Described in: European Patent No 0165919 |
| F | HCl | S | $^1$H-NMR(DMSO): 0.90(t, 3H); 1.70–2.05(m, 4H); 2.45(t, 2H); 2.85(m, 2H); 3.62(s, 3H); 3.70(dd, 1H); 7.60(s, 1H); 8.05(s, 1H); 8.80(broad s, 1H); 9.40(broad s, 1H). MS (LC/MS APCI+): 203($MH^+$). |
| G | HCl | S | $^1$H-NMR(DMSO): 0.90(t, 3H); 1.20(d, 6H); 1.70–2.05 (m, 4H); 2.40(t, 2H); 2.85(m, 2H); 3.65(dd, 1H); 4.90(hept, 1H); 7.65(s, 1H); 8.05(s, 1H); 8.70–9.80(broad s, 2H). MS (LC/MS APCI+): 231($MH^+$). |

TABLE 3-continued

| Compound No. | Salt | Configuration | Analysis/Reference |
|---|---|---|---|
| H | HCl | S | $^1$H-NMR(DMSO): 0.89(t, 3H); 1.40(s, 9H); 1.70–2.00 (m, 4H); 2.32(t, 2H); 2.80(m, 2H); 3.67(dd, 1H); 7.66(s, 1H); 8.09(s, 1H); 8.50–9.90(broad d, 2H). MS (LC/MS APCI+): 245(MH$^+$) |
| I | HCl | S | $^1$H-NMR(DMSO): 0.90(t, 3H); 1.35(t, 2H); 1.50 (s, 6H); 1.55–1.75(m, 6H), 1.75–2.05(m, 7H); 2.40(t, 2H); 2.85(m, 2H); 3.65(dd, 1H); 4.07(t, 2H); 7.60(s, 1H); 8.07(s, 1H); 8.80(broad s, 1H); 9.50(broad s, 1H). MS (LC/MS APCI+): 351(MH$^+$) |
| J | HCl | S | $^1$H-NMR(DMSO): 0.91(t, 3H); 1.50–2.10(m, 12H); 2.37(t, 2H); 2.82(m, 2H); 3.68(dd, 1H); 5.07(m, 1H); 7.62(s, 1H); 8.10(s, 1H); 8.80 (broad s, 1H); 9.60(broad s, 1H). MS (LC/MS APCI+): 257(MH$^+$) |
| K | HCl | S | $^1$H-NMR(DMSO): 0.80–0.95(m, 6H); 1.35–1.45 (m, 2H); 1.45–1.65(q, 2H); 1.70–2.10(m, 4H); 2.40(t, 2H); 2.85(m, 2H); 3.70(dd, 1H); 4.05(t, 2H); 7.60(s, 1H); 8.10(s, 1H); 8.80(broad s, 1H); 9.60(broad s, 1H). MS (LC/MS APCI+): 245(MH$^+$) |
| L | HCl | S | $^1$H-NMR(DMSO): 0.80–0.95(m, 6H); 1.20–1.40 (m, 10H); 1.50–1.65(m, 2H); 1.70–2.05(m, 4H); 2.43(t, 2H); 2.83(m, 2H); 3.71(dd, 1H); 4.01(t, 2H); 7.62(s, 1H); 8.07(s, 1H); 8.80(broad s, 1H); 9.50(broad s, 1H). MS (LC/MS APCI+): 301(MH$^+$) |
| M | HCl | S | $^1$H-NMR(DMSO): 0.80–0.95(m, 9H); 1.70–2.05 (m, 5H); 2.44(t, 2H); 2.82(m, 2H); 3.66(dd, 1H); 3.80(d, 2H); 7.60(s, 1H); 8.03(s, 1H), 8.80 (broad s, 1H); 9.50(broad s, 1H). MS (LC/MS APCI+): 245(MH$^+$) |
| N | HCl | S | $^1$H-NMR(DMSO): 0.90(t, 3H); 1.70–2.05(m, 4H); 2.54(m, 2H); 2.84(m, 2H); 3.86(dd, 1H); 5.10 (s, 2H); 7.30–7.45(m, 5H); 7.62(s, 1H); 8.07(s, 1H), 8.85(broad s, 1H); 9.60(broad s, 1H). MS (LC/MS APCI+): 279(MH$^+$) |
| O | HCl | S | $^1$H-NMR(DMSO): 0.80–0.95(m, 9H); 1.20–1.40 (m, 8H); 1.60(m, 1H); 1.70–2.05(m, 4H); 2.44(t, 2H); 2.82(m, 2H); 3.70(dd, 1H); 3.90(d, 2H); 7.60(s, 1H); 8.10(s, 1H), 8.70(broad s, 1H); 9.60(broad s, 1H). MS (LC/MS APCI+): 301(MH$^+$) |
| P | HCl | S | $^1$H-NMR(DMSO): 0.80–0.95(m, 6H); 1.60(m, 2H); 1.70–2.10(m, 4H); 2.45(t, 2H); 2.85(m, 2H); 3.70(dd, 1H); 3.95(t, 2H); 7.60(s, 1H); 8.10 (s, 1H); 8.80(broad s, 1H); 9.60(broad s, 1H). MS (LC/MS APCI+): 231(MH$^+$) |
| Q | — | S | DSC onset: 100° C. |
| R | — | S | DSC onset: 81° C. |
| S | — | S | DSC onset: 89° C. |
| T | HCl | S | DSC onset: 152° C. |
| U | HCl | S | DSC onset: 84° C. |
| V | — | S | DSC onset: 158° C. |
| W | CF$_3$CO$_2$H | S | DSC onset: 108° C. | d = doublet,
t = triplet,
q = quadruplet,
m = multiplet,
s = singlet,
hept = heptuplet.

NMR (Nuclear Magnetic Resonance) spectra were recorded on a BRUKER AC 250 Fourier Transform NMR Spectrometer or on a BRUCKER ADVANCE DRX 400 Fourier Transform NMR Spectrometer fitted with an Aspect 3000 computer and with a 5 mm $^1$H/$^{13}$C dual probehead. The compound was studied in DMSO-d$_6$ (per-deuterated dimethylsulfoxyde) or in CDCl$_3$ (deuterated chloroform) solution at the probe temperature of 313 K and at a concentration of 20 mg/ml. The instrument was locked on the deuterium signal of DMSO-d$_6$ or CDCl$_3$. Chemical shifts are given in ppm (part per million) downfield from TMS (Tetramethylsilane) taken as internal standard.

Mass spectrometric measurements in LC/MS (Liquid Chromatography/Mass Spectrometry) mode were performed as follows:

As regards HPLC (High Performance Liquid Chromatography) conditions, analyses were performed using a WATERS Alliance HPLC system mounted with an INERTSIL CHROMPACK 3 ODS, DP 5 µm, 250×4.6 mm column.

The gradient ran from 100% solvent A (acetonitrile, water, TFA fluoroacetic acid) (10/90/0.1, v/v/v)) to 100% solvent B (acetonitrile, water, TFA (90/10/0.1, v/v/v)) in 7 min with a hold at 100% B of 4 min. The flow rate was set at 2.5 ml/min and a split of 1/10 was used just before Atmospheric Pressure Ionisation (API) source. The chromatography was carried out at 30° C.

MS Conditions:

Samples were dissolved in acetonitrile/water (70/30, v/v) at the concentration of about 250 µgr/ml. API spectra (+or −) were performed using a FINNIGAN (San Jose, Calif., USA) LCQ ion trap mass spectrometer. Atmospheric Pressure Chemical Ionisation (APCI) source operated at 450° C. and the capillary heater at 160° C. ESI (Electrospray ionisation) source operated at 3.5 kV and the capillary heater at 210° C.

Mass spectrometric measurements in Electron Impact/Direct Introduction Probe (EI/DIP) mode were performed as follows: samples were vaporized by heating the probe from 50° C. to 250° C. in 5 min. EI (Electron Impact) spectra were recorded using a FINNIGAN (San Jose, Calif., USA) TSQ 700 tandem quadrupole mass spectrometer. The source temperature was set at 150° C.

Chromatographic separations are performed on silicagel 60 Merck, particle size 15–40 µm, reference 1.15111.9025.

Melting points are the onset temperature as determined by DSC (Differential Scanning Calorimetry) on a Perkin Elmer DSC 7.

EXAMPLE 5

Pharmacological test to evaluate the anticonvulsant potency of the compounds of formula (I) or (II):

In order to study the activity of the compounds of formula (I) and (II) including the (S) and (R) forms of ethyl 4-{[1-(aminocarbonyl)propyl]amino}butanoate, as anticonvulsant, the applicant performed out a series of experiments based on the audiogenic seizures test in mice.

The objective of the following pharmacological test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. and Schmidt D., Epilepsy Res. (1998), 2, p. 145–181; Buchhalter J. R., Epilepsia (1993), 34, S31–S41).

Male or female genetically sound-sensitive mice (14–28 g; N=10), derived from a DBA (Dilute Brown Agouti) strain originally selected by Dr. Lehmann of the Laboratory of Acoustic Physiology (Paris) and bred in the UCB Pharma Sector husbandry unit since 1978, were used. The experimental design consisted of several groups, one group receiving the vehicle control and the other groups different doses of the test-compound. The compounds were administered intraperitoneally 60 minutes before the induction of audiogenic seizures. The range of the doses administered had a logarithmic progression, generally between 1.0E-5 mol/kg and 1.0E-3 mol/kg, but lower or higher doses were tested if necessary.

For testing, the animals were placed in small cages, one mouse per cage, in a sound-attenuated chamber. After a period of orientation of 30 seconds, the acoustic stimulus (90 dB, 10–20 kHz) was delivered for 30 seconds via loud speakers positioned above each cage; During this interval, the mice were observed and the presence of the 3 phases of the seizure activity, namely wild running, clonic and tonic convulsions, was recorded. The proportion of mice protected against wild running, clonic and tonic convulsions, respectively, was calculated.

For active compounds, an $ED_{50}$ value, i.e. the dose producing 50% protection relative to the control group, together with 95% confidence limits, was calculated using a Probit Analysis (SAS/STATR Software, Version 6.09, PROBIT procedure) of the proportions of protected mice for each of the 3 phases of the seizure activity.

In the Table 5 below, the best results are shown, but they do not limit the present invention. Compounds with smaller mean effective dose ($ED_{50}$) levels are more potent as anticonvulsants.

TABLE 5

| Compound No. | Clonic Convulsion ($ED_{50}$) moles/kg |
|---|---|
| C | 3.2E−04 |
| D | 6.8E−05 |
| F | 1.6E−04 |
| G | 1.5E−04 |
| H | 5.2E−04 |
| I | 1.3E−04 |
| J | 3.4E−04 |
| K | 1.0E−03 |
| L | 1.6E−04 |
| M | 3.6E−04 |
| N | 2.2E−04 |
| O | 1.2E−04 |
| P | 2.0E−04 |
| W | 5.4E−04 |

The present invention has been described in an illustrative manner, and it is to be understood that the terminology used herein is intended to be in the nature of description rather than of limitation.

Many modifications and variations of the present invention are possible in light of the above teachings. Therefore, it is to be understood that within the scope of the appended claims, the invention may be practised otherwise than as specifically described.

The invention claimed is:

1. A method for treating epilepsy, migraine, bipolar disorders, chronic pain or neuropathic pain in a mammal in need of such treatment, comprising administering a therapeutic dose of at least one compound according to formula (I)

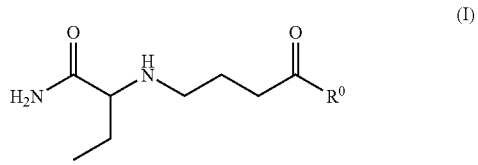

including geometrical isomers, enantiomers, diastereomers, racemates, and pharmaceutically acceptable salts or prodrugs thereof, wherein:

$R^0$ is selected from the group consisting of —$OR^1$, —$SR^1$ or —$NR^2R^1$;

$R^1$ and $R^2$ are independently selected from the group consisting of hydrogen, alkyl, alkenyl, alkynyl, cycloalkyl, cycloalkenyl, heterocycle, aryl, arylalkyl, acyl derivatives, imidoyl, amido, ester, oxo and -(L)-$R^3$ or together are -$L^2$-; if $R^0$ is —$NR^2R^1$ then $R^1$ may also be oxy derivatives or amino derivatives;

R³ is selected from the group consisting of cycloalkyl, cycloalkenyl, heterocycle, aryl, oxy derivatives, thio derivatives, amino derivatives, acyl derivatives, acyloxy derivatives, ether, imidoyl, amido, amidooxy, ester, esteroxy, sulfinyl, sulfonyl;

L¹ is a straight or branched alkylene, alkenylene, alkynylene;

L² is a straight or branched alkylene, alkenylene, alkynylene, or one of the foregoing in which one or more methylenes are replaced by —O—, —S— or —NH—.

2. A method according to claim 1 wherein the at least one compound is the (S) or (R) isomer of formula (II)

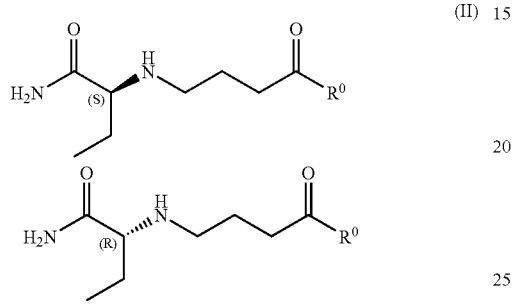

3. A method according to claim 1, wherein the at least one compound is the (S) isomer of formula (II)

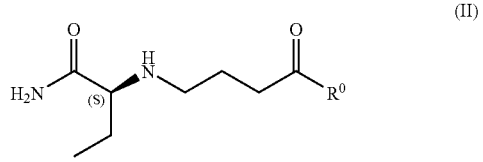

including pharmaceutically acceptable salts or prodrugs thereof, wherein:

R⁰ is —OR¹ or —SR¹

R¹ is selected from the group consisting of (C₁–C₈) alkyl, (C₁–C₁₀) cycloalkyl, C₆ aryl, and L¹-R³;

L¹ is a (C₁–C₇) alkylene;

R³ is (C₁–C₁₀) alkyl, (₁–₁₀) cycloalkyl, or C₆ aryl.

4. A method according to claim 1, wherein the at least one compound is selected from the group consisting of:

4-{[(1S)-1-(aminocarbonyl)propyl]amino}butanamide,
4-{[(1S)-1-(aminocarbonyl)propyl]amino}butanoic acid,
methyl 4-{[(1S)-1-(aminocarbonyl)propyl]amino}butanoate,
isopropyl 4-{[(1S)-1-(aminocarbonyl)propyl]amino}butanoate,
tert-butyl 4-{[(1S)-1-(aminocarbonyl)propyl]amino}butanoate,
2-(1-adamantyl)ethyl 4-{[(1S)-1-(aminocarbonyl)propyl]amino}butanoate,
cyclopentyl 4-{[(1S)-1-(aminocarbonyl)propyl]amino}butanoate,
butyl 4-{[(1S)-1-(aminocarbonyl)propyl]amino}butanoate,
octyl 4-{[(1S)-1-(aminocarbonyl)propyl]amino}butanoate,
isobutyl 4-{[(1S)-1-(aminocarbonyl)propyl]amino}butanoate,
benzyl 4-{[(1S)-1-(aminocarbonyl)propyl]amino}butanoate,
2-propylpentyl 4-{[(1S)-1-(aminocarbonyl)propyl]amino}butanoate,
propyl 4-{[(1S)-1-(aminocarbonyl)propyl]amino}butanoate,
S-isopropyl 4-{[(1S)-1-(aminocarbonyl)propyl]amino}butanethioate and the pharmaceutically acceptable salts and prodrugs thereof.

5. The method of any of claims 1–3 wherein the at least one compound is ethyl 4-{[1-(aminocarbonyl)propyl]amino}butanoate and pharmaceutically acceptable salts and prodrugs thereof.

6. The method of claim 5 wherein the pharmaceutically acceptable salt is the hydrobromide salt or the hydrochloride salt.

7. A method according to any of claims 1–4, wherein the pharmaceutically acceptable salt is the hydrobromide salt or the hydrochloride salt.

8. The method of claims 1–4 wherein migraine, chronic pain or neuropathic pain are treated.

9. The method of claims 5 wherein migraine, chronic pain or neuropathic pain are treated.

* * * * *